United States Patent [19]
Houston et al.

[11] Patent Number: 5,166,133
[45] Date of Patent: Nov. 24, 1992

[54] METHOD FOR INHIBING ADHESION OF WHITE BLOOD CELLS TO ENDOTHELIAL CELLS

[75] Inventors: L. L. Houston, Oakland; David Y. Liu, Palo Alto; Zehra Kaymakcalan, El Cerrito, all of Calif.

[73] Assignee: Cetus Corporation, Emeryville, Calif.

[21] Appl. No.: 700,526

[22] Filed: May 14, 1991

Related U.S. Application Data

[63] Continuation-in-part of Ser. No. 687,300, Apr. 17, 1991, abandoned.

[51] Int. Cl.$^5$ .................. A61K 37/02; A61K 37/64
[52] U.S. Cl. .................................................. 514/8
[58] Field of Search ........................................ 518/8

[56] References Cited

U.S. PATENT DOCUMENTS 4,485,100 11/1984 Hochstrasser et al. .

FOREIGN PATENT DOCUMENTS 255011 2/1988 European Pat. Off. .

OTHER PUBLICATIONS

Akerstrom et al., 1990, TIBS, 15:240-243.
Diarra-Mehrpour, et al., 1989, Eur. J. Biochem. 179:147-154.
Goodman et al, "The Phamacological Basic of Therapy" (7th Edition) MacMillan Publishing Co., pp. 675-676.

Primary Examiner—Merrell C. Cashion, Jr.
Assistant Examiner—Choon Koh
Attorney, Agent, or Firm—Philip L. McGarrigle

[57] ABSTRACT

Proteins are described that affect adhesion of white blood cells (WBCs) to endothelial cells (ECs). The proteins include inter-$\alpha$-trypsin inhibitor, $\alpha_1$-M, and HI-30. When administered in therapeutically effective amounts, these proteins can alter adhesion between WBCs and ECs to ultimately prevent inflammatory-type diseases.

7 Claims, 3 Drawing Sheets

| POOL | | CONCEN-TRATION (mg/ml) | VOL. (ml) | TOTAL PROTEIN | PERCENT RECOVERY PROTEIN | ACTIVE DILUTION | UNITS/ml | TOTAL UNITS | PERCENT RECOVERY UNITS | SPECIFIC ACTIVITY (U/mg) | FOLD PURIFICA-TION |
|---|---|---|---|---|---|---|---|---|---|---|---|
| CRUDE | | 8.91 | 460 | 4100 | 100 | 10 | 400 | 1.8e5 | 100 | 44 | 1 |
| MONOQ | 2 | 1.74 | 125 | 217 | 5.3 | 10 | 1000 | 1.2e5 | 67 | 576 | 13 |
| S-200 | 2A | 0.44 | 39 | 17 | 0.41 | 500 | 50,000 | 1.95e6 | 1083 | 1.15e5 | 2614 |
| IEF | 2AI | 0.50 | 9 | 4.5 | 0.11 | 1000 | 100,000 | 9e5 | 500 | 2e5 | 4545 |
| HPEC | 2AIa | 0.15 | 2.6 | 0.4 | 0.01 | 200 | 20,000 | 5.2e5 | 289 | 13e5 | 29545 |

SUMMARY OF PURIFICATION FOR FRACTION 2AIa

FIG. 3

METHOD FOR INHIBING ADHESION OF WHITE BLOOD CELLS TO ENDOTHELIAL CELLS

This application is a continuation-in-part of Ser. No. 07/687,300, filed Apr. 17, 1991, abandoned.

FIELD OF THE INVENTION

The present invention relates to a process for inhibiting the adhesion between white blood cells and endothelial cells. More specifically, the present invention is a process to prevent white blood cells from attaching to the interior of blood vessels to ultimately prevent them from causing and participating in the inflammatory response.

BACKGROUND OF THE INVENTION

White blood cells can protect the body against various microbial infections as well as diseases such as cancer. However, when white blood cells adhere to endothelial cells on the lumenal site of blood vessels, migrate to body tissues and accumulate there, they often cause damage, swelling, pain, and inflammation. For example, rheumatoid arthritis occurs when white blood cells enter the joints and attack the tissues. It is believed that several molecules on white blood cells recognize their receptors on the surface of the endothelial cell, allowing them to migrate through the blood vessel wall to the site of inflammation. These cell surface molecules on leukocytes and endothelial cells are called cell adhesion receptors. It is believed that if the recognition between these cellular receptors can be blocked, the inflammatory response can be reduced or eliminated.

Different adhesion receptors are presented on the endothelial cell surface at different times and may be recognized by different types of white blood cells. It is possible that two or more receptors may work together to perform this task. Several molecules are already known to act in this fashion.

Many endothelial cell receptors appear to belong to one of two structural supergene families. The Ig superfamily includes ICAM-1 (CD54) and VCAM-1 because of their structural similarity to antibodies. Members of this family interact with receptors on white blood cells known as integrins (CD11/CD18, and VLA-4). The other class, which includes ELAM-1 and GMP-140, are known as LEC-CAMS or selectins. It is believed that they interact with various oligosaccharides on CD15 molecule that is located on white blood cell surfaces. Another member of the LEC-CAM family is the homing receptor (Mel-14, gp90, and Leu-8) located on the surface of leukocytes and recognizes an unidentified molecule on the endothelial cell.

Accordingly, there is a need to interfere with the interaction between white blood cells and endothelial cells to prevent various disease states, for example, rheumatoid arthritis, atherosclerosis, acute and chronic inflammation, arthritis, adult respiratory distress system, autoimmune diseases, and certain cancers. The present inventors have identified several protein compounds that are effective in interfering with white blood cell adhesion to endothelial cells. Those compounds are discussed below.

SUMMARY OF THE INVENTION

The present invention is a method for altering white blood cell adhesion to endothelial cells. The method comprises administering a therapeutically effective amount of a compound selected from the group consisting of $\alpha$1-microglobulin, HI-30, or the combination of both, which will be called inter-$\alpha$-trypsin inhibitor light chain, to a mammal. The reactive compound may include only the amino acids that comprise the primary sequence of these molecules, the carbohydrates that may be attached to them, or a combination of the carbohydrates and the polypeptide sequences. Preferably, the endothelial cells are on the inside of a blood vessel and the compound concentration is between 10 $\mu$g/ml and 5,000 $\mu$g/ml, more preferably to between 100 $\mu$g/ml and 500 $\mu$g/ml. Preferably, the white blood cells are monocytes, neutrophils and lymphocytes.

Among other factors, the present inventors have discovered that $\alpha$1-microglobulin inhibits adhesion of white blood cells to endothelial cells. This inhibition is important because disease states caused by infiltration or accumulation of white blood cells may be therapeutically treated by $\alpha$1-microglobulin or its related compounds or appropriate fragments of them. These disease states include sepsis, inflammation, arthritis, atherosclerosis, autoimmune diseases, rheumatoid arthritis, acute and chronic inflammation, acute respiratory distress syndrome, ischemia/reperfusion injury, inflammatory bowel disease, hemolytic transfusion reaction, certain cancers, transplation, trauma (e.g. burn), among others.

BRIEF DESCRIPTION OF THE DRAWINGS

FIG. 3 summarizes the purification of fraction 2AI from human urine.

DETAILED DESCRIPTION OF THE INVENTION

Figure 1:
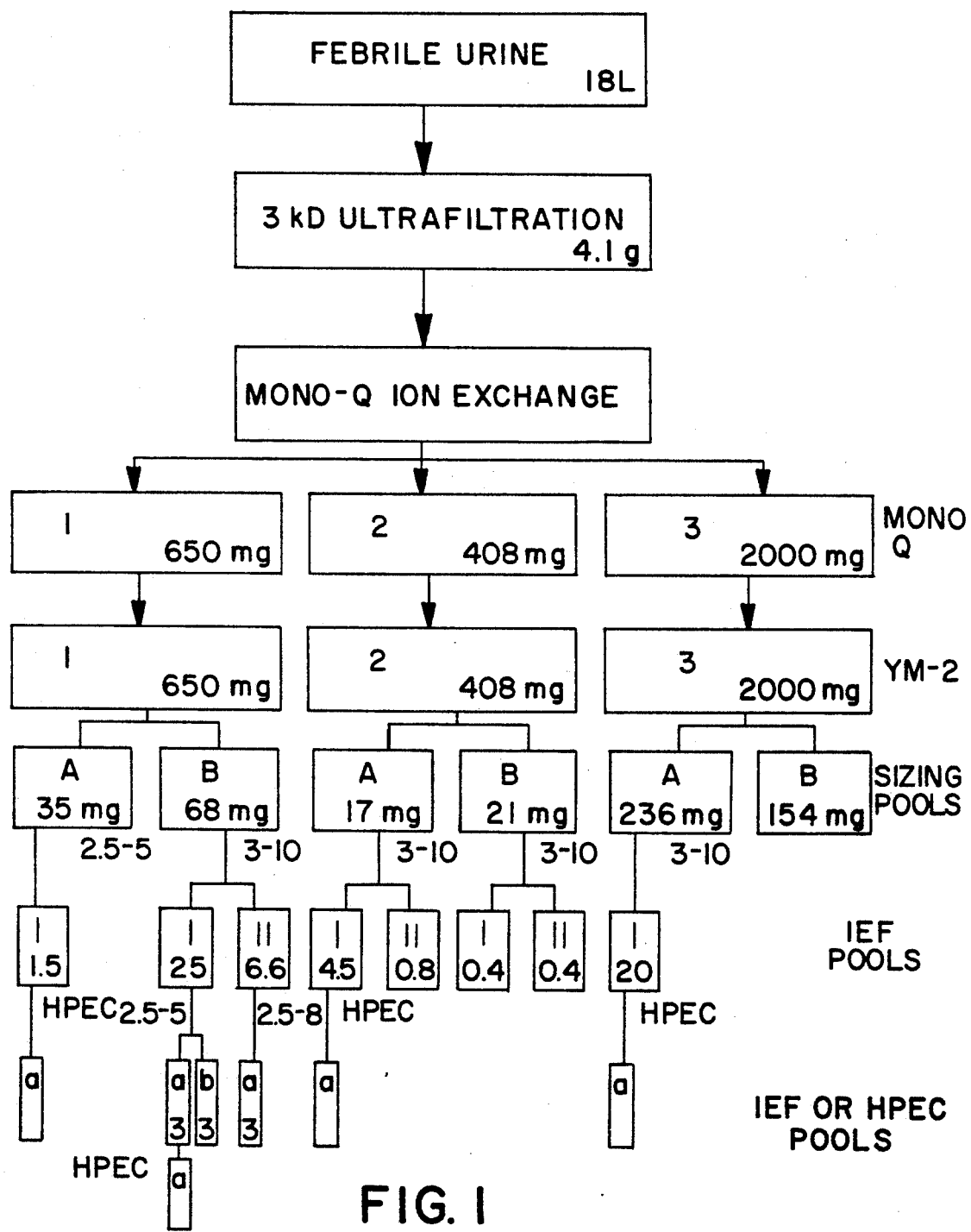
FIG. 1 describes the purification scheme that was used to obtain the present proteins from human urine.

Applicants have discovered that $\alpha$1-microglobulin ($a_1$-M or HC) can interfere with white blood cell adhesion to endothelial cells on the interior of blood vessels. If white blood cells can be prevented from attaching to the receptors on endothelial cells, then they may be prevented from migrating into surrounding tissues where they can cause deleterious effects, such as inflammation. Other compounds that should also be useful to reduce white blood cell adhesion to endothelial cells are HI-30, and inter-$\alpha$-trypsin inhibitor (ITI) light chain (which is the combination of both HI-30 and $a_1$-M). They appear to be related to each other and $a_1$-M by virtue of their genetic relationship as inter-$\alpha$-trypsin inhibitor light chain DNA contains information for both $a_1$-M and H1-30 (even though the ITI light chain is normally cleaved to liberate $a_1$-M). Furthermore, the reactive compound may include only the amino acids that comprise the primary sequence of these molecules, the carbohydrates that may be attached to them, or a combination of the carbohydrates and the polypeptide sequences.

Inter-$\alpha$-Trypsin Inhibitor

ITI (often called I$\alpha$T) can be isolated by affinity chromatography as described by Dubin et al., 1990, *Prep. Biochem.*, 20:63–74. When isolated from human plasma, this serine protease inhibitor has a molecular weight that has been variously reported as 180,000 or 220,000. A series of antibodies produced against smaller proteins cross react with ITI, indicating that the larger protein is cleaved by proteases into fragments.

The physiological function of ITI is not known although it has been described as an in vitro inhibitor of proteases, such as elastase and trypsin. Its structural complexity is reflected in the genes that code for ITI. Four genes, which are distributed among three different chromosomes, specify 3 heavy chains and 1 light chain code for the heavy chains of ITI and are called $H_1$, $H_2$, and $H_3$. The heavy chains have molecular weights of 92,000, 98,000, and 107,000, respectively. There is internal homology within the H chains, but there is no homology between the light and heavy chains. The two heavy chains have the following core sequence:

GGTNINEALLRAIFILNEANNLGLLDPNSVSLIILVSDGDPTVGELKLSKIQKNVKENIQ (SEQ ID NO. 1)
DNISLFSLGMGFDVDYDFLKRLSNENHGIAQRIYGNQDTSSQLKKFYNQVSTPLLRNVQF
NYPHTSVTDVTQNNFHNYFGGSEIVVAGKFDPAKLDQIESVITATSANTQLVLETLAQMD
DLQDFLSKDKHADPDFTRKLWAYLTINQLLEARSLAPTAAAKRRITRSILQMSLDHHIVT
PLTSLVIENEAGDERMLADAPPQDPSCCSGALYYGSKVVPDSTPSWANPSATPVISMLAQ
GSQVLESTPPPHVMRVENDPHSIIYLPKSQKNICFNIDSEPGKILDLASDPESGIVVNGQ
LVGAKKPNNGKLSTYFGKLGFYFQSEDIKIEISTETITLSHGSSTFSLSWSDTAQVTNQR

One of the heavy chains terminates at amino acid 383 and a third heavy chain is extended at N and C termini of the core, as shown below.

NIRTWRNDLFQLQKHRLQIAKRYIEKIQPS ... core ... EPKIHIFNERPGKDPEKPEASMEV (SEQ ID NO. 2)
KGQKLIITRGLQKDYRTDLVFGTDVTCWFVHNSGKGFIDGHYKDYFVPQLYSFLKRPXRFIVWE as shown by Bourguignon et al., 1989, *J. Biochem.*, 261:305–308. The ITI light chain gene is most germane to the results that have been obtained by the present inventors, as the light chain gene specifies sequences of two proteins, α1-microglobulin and HI-30, which we have identified and purified from febrile urine samples.

The exact quaternary structure of ITI still is confusing in many respects. Most of the published work is consistent with the presence of 1 H chain and 1 L chain in ITI, although it has been suggested that 2 light chains may be included (Salier, J. P. et al., 1987, *PNAS (U.S.A.)*, 84:8272–8276). Another report suggests that a pre-ITI species exists that has 2 heavy chains and 1 light chain. The H and L chains are synthesized separately. Synthesis of the L chain has been shown to occur in human liver and rat kidney, as well as human lung and skin fibroblasts.

Carbohydrate may link the light chain of inter-α-trypsin inhibitor to the heavy chain as described in Enghild, J. J., et al., 1989, *J. Biol. Chem.*, 264:1428–11435. Enghild et al. argued that a pre-ITI is composed of one light chain and one heavy chain that is different from the two ITI chains that are found associated with one light chain. In both cases, Potempa, J., et al., *J. Biol. Chem.*, 264:15109–15114, suggested that carbohydrate links HI-30 to the heavy chain.

The light chain contains the sequences for two proteins arranged as follows:

ITI Light Chain: The ITI light chain of inter-α-trypsin inhibitor is coded by a single gene in humans. The gene contains 10 exons and 9 introns in a 20 kbp sequence of the genome as described by Diarra-Mehrpour, M., et al., 1990, *Eur. J. Biochem.*, 191:131–139. It has been shown that the gene that codes for the light chain (which has been called the IαTI Light Chain) contains the sequences for two different proteins: $\alpha_1$-M and a smaller protein called HI-30. (See Kaumeyer, J. F. et al., 1986, *Nucleic Acids Res.*, 14:7839–7850 and Bourguignon, J., et al., 1985, *Biochem. Biophys. Res. Commun.*, 131:1146–1153) Both $\alpha_1$-M and HI-30 are produced from inter-α-trypsin inhibitor light chain. $\alpha_1$-M and HI-30 are thought to be produced by proteolysis of the ITI light chain. The sequence that Diarra-Mehrpour report for the ITI light chain is:

| Exon 1 | MRSLGALLLLLSACLAVSAGPVPTPPDNIQVQENFNISRIY (SEQ ID NO. 3) |
|---|---|
| Exon 2 | GKWYNLAIGSTCPWLKKIMDRMTVSTLVLGEGATEAEISMTSTRWR (SEQ ID NO. 4) |
| Exon 3 | KGVCEETSGAYEKTDTDGKFLYHKS (SEQ ID NO. 5) |
| Exon 4 | KWNITMESYVVHTNYDEYAIFLTKKFSRHHGPTITAKLY (SEQ ID NO. 6) |
| Exon 5 | GRAPQLRETLLQDFRVVAQGVGIPEDSIFTMADR (SEQ ID NO. 7) |
| Exon 6 | GECVPGEQEPEPILIP (SEQ ID NO. 8) |
| | \|cleavage site to release $\alpha_1$-M from HI-30 |
| Exon 7 | RVRRAVLPQEEEGSGGGQLVTEVTKKE (SEQ ID NO. 9) |
| Exon 8 | DSCQLGYSAGPCMGMTSRYFYNGTSMACETFQYGGCMGNGNNFVTEKECLQTCRTV (SEQ ID NO. 10) |
| Exon 9 | AACNLPIVRGPCRAFIQLWAFDAVKGKCVLFPYGGCQGNGNKFYSEKECREYCGVPGD (SEQ ID NO. 11) |
| Exon 10 | GDEELLRFSN (SEQ ID NO. 12) |

Exons 1–6 code for $\alpha_1$-M and exons 7–10 code for HI-30. Domain I of HI-30 is specified by exon 8, and domain II is specified by exon 9. Domain I contains the site that inhibits leukocyte elastase and domain II inhibits trypsin and chymotrypsin. (See also Diarra-Mehrour, et al., 1990, *Eur. J. Biochem.*, 191:131–139.)

α1-Microglobulin

The lipocalin protein family contains $a_1$-microglobulin ($\alpha_1$-M, often called HC), a protein whose physiological function has not been defined (see Akersrom and Loydberg, 1990, *TIBS*, 15:240–243) $\alpha_1$-M is related to

```
                              HI-30
|----- leader -----|----- α1-microglobulin ----|---- domain I ----- domain II ----|
```

Three separate mRNAs described in Diarra-Mehrpour, M., et al., 1990, *Eur. J. Biochem.*, 179:147–154, β-lactoglobulin, insect bilin-binding proteins, and retinol-binding proteins. These proteins are structurally related to each other by a unique form referred to by Akerstrom and Loydberg as a coffee filter because eight β strands are arranged to form a hollow cone that resembles a coffee filter. $\alpha_1$-M contains a polypeptide sequence, whose sequence is known, and at least one carbohydrate moiety, whose sequence is not known. Activities that have been ascribed to $\alpha_1$-M include inhibition of antigen stimulation of lymphocytes and generic effects on inhibition of granulocyte migration.

$\alpha_1$-M is an acute phase reactant and is a 31,000 molecular weight glycoprotein that has been detected in urine, cerebrospinal fluid, and serum. When $\alpha_1$-M is isolated from urine, it has a unique amino acid sequence, but is very heterogeneous in its charge properties (Lopez, C., et al., 1984, Arch. Biochem. Biophys., 228:544–554). The protein binds a yellow-brown chromophore and it is also complexed with IgA. One chromophore that has been identified is retinol. The complex of $\alpha_1$-M and IgA has been reported to contain 2 L chains and 1 H chain of IgA and 1 peptide that contains H chain α and $\alpha_1$-M epitopes as described in Grubb, A. O., et al., 1983, J. Biol. Chem., 258:14698–14707. Others (Akerstrom & Lodgberg, 1990, TIBS, 15:240–242; and Salier et al., 1990, TIBS, 15:435–439) show that the structure contains an IgA molecule bound to 1 molecule of $\alpha_1$-M. This complex inhibits the chemotactic response of neutrophils Mendez et al., 1986, PNAS (U.S.A.), 83:1412–1475. cDNA that specifies $\alpha_1$-M has been described in Traboni, C., et al., 1986, Nucleic Acids Res., 14:6340.

Tejler and Grubb, 1976, BBA, 479:82–94 showed that HC is electrophoretically heterogeneous on isoelectric focusing. HC is contained in many bands in the acid region (below pH 3–4.4) and the desialydated protein has higher isoelectric points (between pH 4.2–5.3). Tejler and Grubb found about 10 μg of $\alpha_1$-M/ml of normal urine and about 600 μg/ml was found in urine from patients with renal failure.

The concentration of $\alpha_1$-M in plasma from blood donors is about 20 μg/ml and the IgA-$\alpha_1$-M complex is about 290 μg/ml as shown by Mendez, E., et al., supra. According to Takagi et al., 1980, Clin. Chem. Acta, 108:277–831, $\alpha_1$-M concentration does not change in a variety of disorders. For example, in patients with kidney failure, the plasma concentration increases about 8-fold, but the IgA-$\alpha_1$-M complex concentration decreases to about 150 μg/ml. Synovial fluid from patients with rheumatoid arthritis contains about 12 μg/ml of $\alpha_1$-M and about 31 μg/ml of the IgA-$\alpha_1$M complex. According to Salier et al., 1990, TIBS 15:435–439 "$\alpha_1$-M has never been found in the IαTI molecule or its derivatives and is apparently completely unrelated to protease inhibitors".

HI-30

The sequence homology within HI-30 suggested (to Salier, et al., TIBS supra) that HI-30 contains two homologous domains that are inhibitory sites for elastase, trypsin and chymotrypsin. Salier, et al., implied that the elastase site and the trypsin/chymotrypsin sites are separate sites and refer to work reported by Reisinger, et al., 1985, Biol. Chem. Hoppe-Seyler, 366:479–483 and Wachter, E. and Hochstrasser, K., 1979, Hoppe-Seyler's Z. Physiol. Chem., 360:1305–1311. Diarra-Mehrpour et al., supra, repeat the notion that HI-30 contains two tandem Kunitz-type domains (I and II). Pervaize, S. and Brew, K., 1987, FASEB. J., 1:209–214 suggested that HI-30 was a member of the lipocalin superfamily.

The notion of two domains that have different inhibitory activities was further supported by Swaim, M. W. and Pizzo, S. V., 1988, J. Biochem., 254:171–178. They showed that reaction of ITI with butane-3,3-dione (an arginine specific reagent) completely prevented the modified ITI from inhibiting trypsin and chymotrypsin with only a partial loss of inhibitory ability against elastase and cathepsin G. In contrast, modification with cis-dichlorodiammineplatinum (II), a methionine specific reagent, partially inactivated the inhibitory capability against elastase and cathepsin G, but had no effect against the ability to inhibit trypsin and chymotrypsin.

HI-30 is a fairly stable protein, as its activity survives precipitation with perchloric acid and it can be chromatographed on reverse phase columns with retention of activity.

Although three peptides have been described, the invention encompasses those peptide fragments which are active to accomplish the same effect. The fragments may be discovered by taking different portions of the compounds and screening them in the assays described below. Furthermore, the sequences described above can be modified using standard techniques without changing their effect. Modifications to the primary structure itself, by deletion, addition, or alteration of the amino acids incorporated into the sequence during translation, can be made without destroying the activity of the protein. Preferably, these changes involve conservative modifications in the amino acid sequence. A conservative amino acid alteration is defined as one which does not significantly adversely affect biological activity and involves substitutions of the amino acid.

The precise chemical structure of α1-microglobulin, HI-30, or inter-α-trypsin light chain depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivitization using sugar moieties (glycosylation) or by other supplementary molecules such as lipids, phosphates, acetyl groups and the like. It may also be augmented by conjugation with saccharides or polymeric molecules. Certain aspects of such augmentation are accomplished through post-translational processing systems of the producing host, while other such modifications may be introduced in vitro. In any event, such modifications are acceptable so long as the described biological effects are not significantly adversely affected.

Manufacture $\alpha_1$-M, and HI-30, can be purified from human urine (febrile urine contains higher concentrations of the factors and most of $\alpha_1$-M in serum exists as a complex with IgA). A process is outlined below, and it entails fractionating human febrile urine using ion exchange chromatography, gel filtration, isoelectric focusing, and preparative gel electrophoresis. More specifically, the ion exchange chromatography used Mono-Q columns, the gel filtration used GF-2000 columns or Sephredex-G200, the isoelectric focusing used a Rotofor apparatus, and the preparative gel electrophoresis used an ABI instrument. The purification strategy has been to concentrate the febrile urine, dialyze it against a low ionic strength buffer, and fractionate by charge (ion exchange), by size (gel filtration), by isoelectric point (isoelectric focusing), and by high performance electrophoresis on polyacrylamide gel (HPEC). Further details are shown in the examples below and in FIG. 1. Once the urine is separated using this technique, different protein bands are isolated from the gel electrophoresis stage and tested for their ability to inhibit adhesion of white blood cells to endothelial cells. Other purification processes are shown in Dubin et al., 1990, *Prep. Biochem.*, 20(1):63-74.

The three peptides can be made by methods that are known to those of ordinary skill in the art, such as solid phase synthesis, chemical solution synthesis, or by recombinant means. In the solid phase synthesis process, polystyrene resin is chemically derivatized to contain a reactive group. Then, the amino acid at the carboxy terminus is added to a solution which is in contact with the resin. The amino group and the side chains of all the amino acids that are added to the solution are blocked to prevent reactivity; these bonds must be stable until the blocking agents are removed under the correct conditions. The carboxylic acid end of the amino acid is covalently connected to the resin by a bond that is stable until it is cleaved when the peptide is completed. After the first amino acid is covalently attached to the resin, the solution containing the unreacted components is flushed. Thereafter, another amino acid is contacted with the resin, and it is connected to the amino acid that is attached to the resin. The solution containing the unreacted products is flushed again and the cycle is repeated for each amino acid that is added to the growing peptide. The solid phase system has been automated; an exemplary instrument that is useful to make peptides is the using a Milligen/Biosearch-9500 Automated Peptide Synthesizer. More information on this process can be obtained from Stewart et al., Solid Phase Peptide Synthesis, 2nd Ed., Pierce Chemical Co., U.S. Pat. Nos. 4,839,464, 4,517,686, 4,578,079, 4,589,881, 4,614,517, 4,661,111, and 4,578,079, which are hereby incorporated by reference in their entireties.

The chemical solution synthesis is also a stepwise reaction, however it starts with two amino acids in a solution. As above, some reactive groups are blocked so that they will not interfere with the covalent conjugation between an intended amino and carboxyl group. There action begins when two amino acids are contacted and conjugated at the amino and carboxyl ends with a typical peptide bond. Thereafter, the reaction product is separated from the unreacted and unwanted compounds. This sequence is repeated for each amino acid that is added until the desired peptide is obtained. This method is more fully explained in Mutter et al., 1980, *The Liquid Method for Peptide Synthesis in the Peptides—Analysis, Synthesis, Biology* ed. Gross and Meienhofer, vol. 2 Academic Press, N.Y.

Also, these proteins may be manufactured by recombinant methods (see EP 255,011 which is hereby incorporated by reference in its entirety). To produce a peptide by this method the amino acid sequence would need to be back translated into the appropriate DNA sequence. For example, those sequences disclosed above for the three compounds would be back translated into the human DNA sequence to form a linear chain. Then the DNA sequence would be introduced into a host cell genome or a plasmid, then into the host cell. Thereafter the cell would be manipulated so that the peptide is produced. Depending on the host cell expressing the protein, a leader may be used for secretion and glycosylation. A preferred bacterial host is *E. coli* or Streptomyces, however mammalian and insect host cells may also be used, especially for purposes of glycosylation. See Maniatis et al., Molecular Cloning, 2d Ed, Cold Spring Harbor Laboratory Press (1989). Conditions for fermenting the host cell are known to those with ordinary skill in the art and may be obtained by perusing the appropriate literature (see for example U.S. Pat. Nos. 4,656,132, and 4,894,334 which are hereby incorporated by reference in their entireties). Additionally, once the compounds are made they may be isolated and purified. Methods for isolating and purifying recombinant proteins are also known to those with ordinary skill in the art. Exemplary patents which discuss protein recovery from recombinant cells are U.S. Pat. Nos. 4,748,234 and 4,931,543 which are hereby incorporated by reference in their entireties.

If the peptides are made recombinantly, then alterations in the amino acid sequence could be easily made to beneficially change the properties of the compound. For example the site in $\alpha_1$-M that binds IgA may be eliminated or changed to prevent IgA binding. These amino acid residues can include the 9 amino acids on the carboxy terminal. In any event, it is envisioned that the compounds that are made contain the activities described above and have substantial sequence homology to either ITI light chain, $\alpha_1$-M, and HI-30. Methods to delete, substitute, or otherwise alter the amino acid sequence are known in the art. They include restriction enzyme digestion and site directed mutagenesis. See also U.S. Pat. No. 4,959,314 which is hereby incorporated by reference in its entirety. Other commonly known techniques can be found in Maniatis et al. supra. Additionally, $\alpha_1$-M can be purchased commercially from Fitzgerald Industries International, Chelmsford, Mass.

Assay Methods

Several assays were helpful in assessing potential anti-inflammatory activity.

Leukocyte Preparation/Labelling: Leukocyte adherence can be measured using several assays known in the art, and the preferred assay is described by Charo, et al., 1985, *Blood*, 65:473. Briefly, the assay consists of labelling leukocytes with an appropriate label, incubating them with endothelial cells and determining the number of leukocytes that adhere. Preferably the cells are labelled with a gamma ray emitting isotope and the preferred labels are $^{111}$Indium-oxide or $^{51}$chromium.

Leukocytes may be isolated from human donors using standard techniques. This generally consists of isolating blood in a physiologically balanced salt solution containing an appropriate anticoagulant, and separating the leukocytes by an appropriate separation step, preferably on Ficoll-Hypaque gradients and colloidal silica gradients. Contaminating erythrocytes can be removed by hypotonic lysis. The resulting leukocytes are suspended in a physiologically buffered solution, pH 7.4. The preferred physiological buffered solution is Hank's balanced salt solution that is calcium and magnesium free.

The isolated leukocytes can then be labelled by incubating them for an appropriate time, generally 15 minutes, with the desired radioisotope at a predetermined concentration. The radiolabelled cells are washed to remove unincorporated label, and then suspended in an appropriate solution to perform the adhesion assay described below.

Endothelial Cell Preparation/Culture: Endothelial cells can be prepared from a number of sources and by several techniques known in the art. Preferably they are obtained from human umbilical veins using the procedure of Charo et al., above. Generally, endothelial cells are isolated by enzymatic digestion of the umbilical veins using, preferably, collagenase as described by Jaffe, E. A., et al., 1973, *J. of Clin. Invest*, 52:2745. The cells are grown on an appropriate tissue culture substratum, preferably gelatin-coated surfaces.

The endothelial cells may be grown in a variety of tissue culture media containing appropriate supplements such as an appropriate concentration of fetal calf serum, and other supplements/additives routinely utilized by those skilled in this art that are recognized as being favorable for endothelial cells. The endothelial cells may be passaged with a dilute solution of an appropriate protease, and if desired a metal ion chelator. Preferably a solution consisting of 0.05 to 0.25% trypsin and 0.02% EDTA is used. To ensure that the cells are indeed endothelial cells, they are tested by immunofluorescence for Factor VIII antigen, a known endothelial cell marker.

Leukocyte/Endothelial Cell Adhesion Assay: Leukocyte adherence to endothelial cell monolayers may be determined as follows. Early passage endothelial cells, generally not beyond the fifth passage, are cultured on an appropriate substratum and in a suitable cell culture medium. The culture substratum is preferably pre-coated with an appropriate substance that enhances the adherence of the endothelial cells. Several such substances are known including fibronectin, poly-L-lysine, gelatin and laminin. Fibronectin is preferred. An appropriate culture substratum is a 96 well micro titer plate, and a suitable medium is Medium 199 containing fetal calf serum and other supplements known to be beneficial for the growth and maintenance of endothelial cells that are well known to those skilled in the art. Prior to adding a predetermined number of labelled leukocytes, the endothelial cell monolayer is washed with a physiologically balanced salt solution containing a reduced amount of fetal calf serum, preferably 1%. The preferred solution is RPMI supplemented with 1% fetal calf serum.

The endothelial cell monolayer containing added leukocytes is incubated for a time sufficient to permit maximum adherence of the leukocytes, and preferably this is conducted at 37° C. for 30 minutes in an appropriate cell culture atmosphere. Generally this would consist of growing and incubating the cells for the assay period in 5% $CO_2$, 95% air, and 95% humidity. Next, non-adherent leukocytes are removed by any number of techniques known in the art, and the number of leukocytes adherent to the endothelial cell monolayers determined by measuring the amount of radioisotope associated with the endothelial cell monolayer. Controls are run that take into account basal binding, i.e., binding to endothelial cells not activated with TNF.

The endothelial cells were activated with 125 U/ml of TNF having a specific activity of $2 \times 10^7$ U/mg for at least 4 hours in RPMI with 1% fetal calf serum prior to the addition of the leukocytes. TNF causes the expression of several adhesion molecules on EC surfaces, including ICAM and VCAM. ICAM molecules on endothelial surfaces are receptors for leukocyte integrin binding.

In a typical experiment run in quadruplicate, the assay is highly reliable, giving standard deviations less than 10%, and usually less than 5%, of mean values. Typically the results are expressed as the percent of leukocytes added to the endothelial cells that remain adherent after non-adherent cells have been removed.

Chemotaxis: The materials and methods for ascertaining the chemotactic inhibitory properties of peptides are generally known in the art, and the preferred procedure is described by Capsoni, et al., 1989, *J. of Immunol. Meth.*, 120:125. Generally, chemotaxis is determined by positioning the leukocytes and a chemotactic substance on opposite sides of a membrane in appropriate culture media. The preferred apparatus for doing a chemotaxis assay is produced by Costar Corporation, Cambridge, Mass. and is termed the trans-well cell culture apparatus. The size of the membrane is selected so that the leukocytes do not have unrestricted access to the substance; rather if a chemotactic response is elicited the leukocytes adhere to, and migrate into and through the filter. If a substance is being tested for inhibitory activity this can be achieved by combining it with the leukocytes or the chemotactic substance.

The procedure of Capsoni, et al., above, was followed with the following modifications. Leukocytes may be isolated and labelled with $^{111}$Indium as described for the adhesion assay, above. The cells are resuspended after labelling in an appropriate cell culture medium at about $5 \times 10^6$ cells/ml. Next, a desired amount of the cell suspension is mixed with a predetermined amount of the compounds to be tested for inhibitory activity, and the mixture added to an appropriate filter device. Three μmpore membranes are situated in the wells of a 24 trans-well tissue culture plate. The cell/inhibitory peptide mixture is incubated for a short time at 37° C. to acclimate the cells and to provide sufficient time for them to settle onto the membrane surface. Next, the membrane inserts are set in wells containing cell culture media. The media contains zymosan-activated human serum at about 0.5%. Zymosan activation generates complement-derived chemotactic factors which attract the leukocytes through the pores of the membrane. This media was also prewarmed for an appropriate time prior to addition to the cell culture wells. After a 30 minute incubation period at 37° C., the number of leukocytes that have migrated through the membrane filter, in the presence or absence of inhibitor, is readily determined by counting the amount of $^{111}$Indium present in the media. This may be facilitated by adding an appropriate detergent at an appropriate concentration to the media in the wells prior to removing an aliquot for counting. In this way, the inhibitory activities of the peptide being tested could be determined.

The in vivo model is generally shown in Jutila et al., 1989, *J. of Immun.*, 143:3318-3324 and is specifically as follows. Inflammatory mouse peritonitis model: Mice strain balbc/were given 1 ml of thioglycollate medium by i.p. inoculation to stimulate the invasion of neutrophils into the i.p. cavity. Control mice received no injection or excipient vehicle. In this model, PMNs rapidly invade the i.p. cavity in response to thioglycollate. For the first 3 hours, nearly all of the invading cells are PMNs. Test samples of various materials were injected i.v. into the mice at they same time thioglycollate in given. After 3 hours, mice were killed by cervical dislocation and the peritoneal cavity was lavaged with 10 ml Hanks buffered saline. Samples of the cells were immediately counted to determine the total number of cells/ml in each harvest. Differential nuclear staining was used to determine the number of neutrophils.

Administration

Once the compounds have been made, they can be therapeutically or prophylactically administered to reduce, prevent, or alter the adhesion of white blood cells to endothelial cells, preferably to reduce adhesion between leukocytes to endothelial cells that line blood cell walls. Consequently, the compounds need to be produced, purified and formulated for administration. Once they have been purified, they can be administered by parenteral injection (i.e., intravascular(intraarterial, or intravenous), intramuscular, and subcutaneous), oral and occular and intraocular transdermal administration. Parenteral administration is preferred, and intravascular is more preferred. Methods to effect this administration are known to those of ordinary skill in the art. Additionally, the compounds can be attached to polyethylene glycol, placed into liposomes or microcapsules, or otherwise attached to other soluble or insoluble compounds and systemically or locally introduced into the body. Methods and devices to accomplish these results are known to those of ordinary skill in the art.

Preferably, the compound are therapeutically or prophylactically administered to achieve a concentration between 10 µg/ml and 5,000 µg/ml in the blood, more preferably to between 100 µg/ml and 500 µg/ml in the blood.

$\alpha_1$-M is readily soluble in phosphate buffered saline. However, before administration to patients, formulants may be added to the peptides to make a topical or parenteral formulation. A parenteral, liquid formulation is preferred. For example, these formulants may include polymers, vitamins, carbohydrates, amino acids, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sucrose is most preferred. Sugar alcohol is defined as a $C_4$ to $C_8$ hydrocarbon having an -OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar.

Surfactants that can be added to the formulation are shown in EP Nos. 270,799 and 268,110.

Additionally, the present peptides can be chemically modified by covalent conjugation to a polymer to increase their circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the IL-2. However, it will be understood that the type and amount of the reactive groups may be varied to achieve a covalently conjugated PEG/IL-2 of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution or sterile saline, for example) which may include additional ingredients. Upon reconstitution, the composition is preferably administered to subjects using those methods that are known to those skilled in the art.

The present invention will now be illustrated by reference to the following examples which set forth particularly advantageous embodiments. However, it should be noted that these embodiments are illustrative and are not to be construed as restricting the invention in any way.

EXAMPLE 1

Isolation of Inhibitors of Endothelial Cell Adhesion From Urine

Febrile and non-febrile urine samples were examined for the presence of inhibitors of monocyte adhesion to endothelial cells. The goal was to confirm the presence of inhibitors and to show that the inhibitors can be recovered after chromatography through Mono-Q columns and gel filtration. This was achieved and a stronger signal was received from the febrile urine samples. At least three major regions of activity were found after Mono-Q chromatography. The pool of active fractions that elute first from Mono-Q separation contain two molecular weight species. Additional purification was achieved by isoelectric focusing. We also discovered that the urine samples could be filtered through an Amicon spiral cartridge to reduce the sample volume.

EXAMPLE 2

Isolation of Adhesion Proteins From Febrile Urine

An 18 liter sample of febrile urine collected from two patients at Alta Bates Hospital has been analyzed for the presence of factors that inhibit the adhesion of human monocytes to umbilical vein endothelial cells. Several fractions were identified that inhibit adhesion. Efforts were focused on two of the factors that have low isoelectric points. Some of the fractions were diluted by as much as 15,000 times before activity was lost. However, the concentrations of the factors appears to be low, which is indicative of the presence of highly active factors.

Figure 2:
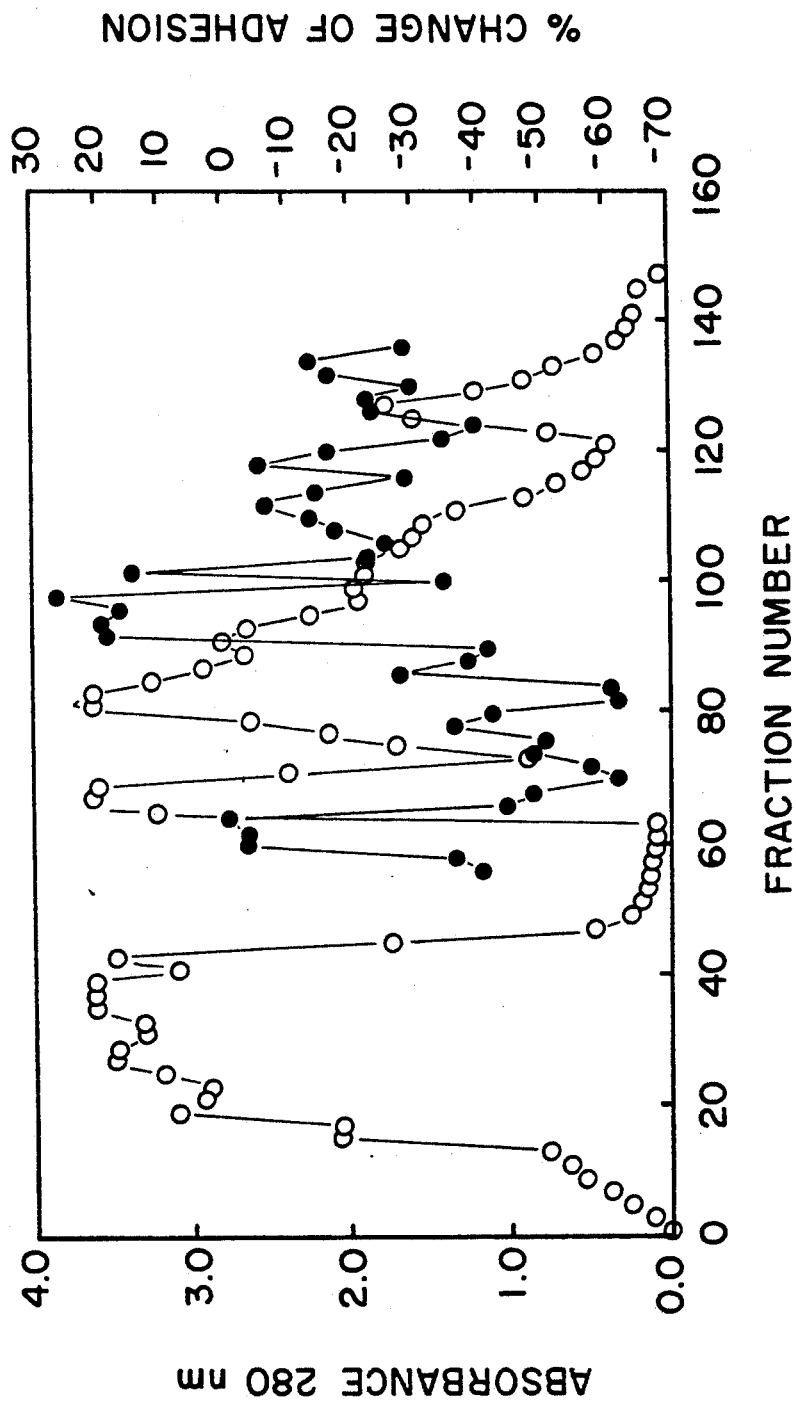
FIG. 2 shows the output from the MONO-Q column and which fractions contained protein (as shown by $A_{280}$ absorbance, open circles) and which showed adhesion inhibition (black circles).

The purification of these fractions follows the broad outline in FIG. 1. The numbers within the boxes are the yields in milligrams of the individual fractions. Febrile urine is collected and stored in a vessel containing benzamidine, sodium azide, and EDTA to inhibit bacterial growth and reduced proteolysis. Ultrafiltration concentrated the proteins on a low molecular weight cutoff membrane that was used to retain any small molecular weight factors. After dialysis, the material was passed over an anion exchange column (Mono-Q) and the adhesion inhibition activity was resolved into three fractions. Fraction 3 was the material that was not retained by the column, and fraction 1 and 2 were eluted in a NaCl gradient. After concentration on a YM-2 membrane, the fractions were passed over a Sephacryl S-200 column to separate the factors on the basis of their sizes. Fraction 1, 2 and 3 each was resolved into two peaks of activity by sizing. In all cases the adhesion assay used human umbilical vein endothelial cells and human monocytes obtained from blood. See FIG. 2 which shows that pool 1 (centered around fraction 67) and pool 2 (centered around fraction 83) inhibited adhesion. The open circles represent the $A_{280}$ absorbance and the black circles represent % change in adhesion.

Isoelectric focusing on the BioRad Rotofor system was used to further analyze the individual fractions from the sizing separation. In addition to separating the factors from contaminants, information was gathered about the isoelectric points of the factors. The following table summarizes the isoelectric points of different fractions.

TABLE 1

| Fraction | Isoelectric Point | Fraction | Isoelectric Point |
|---|---|---|---|
| 1AIa | 4.8 | 2AI | 3-4 |
| 1AIb | 4.8 | 2AII | 6.5 |
| 1BIa | 3.8 | 2BI | 7.5 |
| 1BIb | 4.2 | 2BII | 8.3 |
| 1BIIa | 4.2 | | |

The activity of Pool 1AIa has been detected three consecutive times after separation on HPEC. In addition, two other pools (Pools 2BI and 2BII) contain strong inhibitors of adhesion.

Even though four purification steps have been used, none of the factors are homogeneous. The specific activity of Pool 1AI has increased by about 20,000-fold. If one assumes that an increase of 10-fold is required to reach complete homogeneity, this implies that about 20 μg (1 μg/liter) of the inhibitor was present in the initial crude urine.

Each pool from the Mono-Q anion exchange chromatography appears to contain two inhibitors that differ in size and isoelectric point. A range of isoelectric points from acidic to basic are associated with the inhibitors.

Gel filtration of Pool 2 on a Sepharose S-2000 column resulted in the resolution of two activity peaks (Pool 2A and 2B) that were less active than those found in Pool 1. These pools (2A and 2B) were separately dialyzed and prepared for isoelectric focusing. Because this was the first time that these samples were examined, a wide pH 3-10 gradient was used. Separation of Pool 2B resolved two regions of activity that could be measured at a dilution of 1000-fold. Pool 2A was also resolved into two regions of activity. FIG. 3 summarizes the purification of fraction 2.

EXAMPLE 3

Sequencing

Pool 1AIa was depleted before sequencing. However, we were able to obtain enough material from pool 2AI; therefore, we describe those sequences. It is likely that the pools are related; all containing compounds that are derived from $\alpha_1$-M.

We separated samples of active fractions 2AI and 2AII by SDS-PAGE and individual protein bands were removed from the 2AI gel and sequenced by standard techniques. The sequences that were determined were matched with proteins that are derived from the light chain of inter-α-trypsin inhibitor, as described by Diarra-Mehrpour et al., 1990, *Eur. J. Biochem.*, 191:131-139.

The sequence of inter-α-trypsin inhibitor light chain is compared below to the amino terminal sequences of peptides that were sequenced after SDS-PAGE. A 29,000 molecular weight protein was sequenced from SDS-PAGE that had GPVP-PPDNIQVQENF-IS-IYG (SEQ ID NO. 13) at its amino terminus. The dashes indicate uncertain residues. This sequence is consistent with that of the amino terminal region of $\alpha_1$-M.

A 20,000 molecular weight protein has an amino terminus sequence of AVLPQEEEGGG-GQLV—TKKED (SEQ ID NO. 14). This sequence is consistent with that of the amino terminal region of HI-30.

A 18,000 molecular weight protein had an amino terminus sequence of -TEVTKKEDSSQLLGY—(-SEQ ID NO. 15). This sequence is consistent with the sequence starting at position 17 (i.e., T) in HI-30 and indicates that differences in cleavage exist of the light chain precursors or proteolytic sensitivity of HI-30.

A 18,000 molecular weight protein had an amino terminus sequence of -GMTSR—YN (SEQ ID NO. 16). This sequence is contained near the amino terminus of HI-30 starting at position 37.

A 14,000 molecular weight protein had an amino terminus sequence of VTEVTKKEDSQLGYS (SEQ ID NO. 17). This sequence is contained near the sequence shown above and is consistent with one starting at position 16 in $\alpha_1$-M.

Although statements in the literature indicate that HI-30 is never found in association with $\alpha_1$-M, we have clearly isolated fractions in which both proteins or fragments of those proteins are present.

As stated above, $\alpha_1$-M is known to be a heterogeneous protein. As one example, Tejler and Grubb showed that several distinct bands can be observed on a smeared background when $\alpha_1$-M is run on an isoelectric focusing gel (see FIG. 2 of Tejler and Grubb). The isoelectric points are acidic, below pH 6, and are dependent on the extent of sialydation, as inferred by experiments using neuraminidase.

EXAMPLE 4

Since the active fractions identified above were related to $\alpha_1$M we purchased it from Fitzgerald Industries International, Inc., Chelmsord, Mass. 01824, Lot #A0112901 to test it in our assays. However, it was analyzed for purity first. (A 1 mg/ml solution has faint yellow color.) We analyzed the $\alpha_1$-M by SDS-PAGE and found two bands at approximately 30 kD and two bands at approximately 65 kD. We further analyzed the $\alpha_1$M in HPEC, separated the 30 and 65 kD species, and tested them in the adhesion assay using PMNs and monocytes with ECs. (We tried to sequence the 65 kD fraction, but there was not enough to get any information.) Without wishing to be bound by theory, it is possible that the 65 kD fraction is an aggregated form of $\alpha_1$-M which may or may not be active as an aggregate.

The commercial $\alpha_1$-M was used in the adhesion assay described above to test the effect of $\alpha_1$-M in preventing adhesion. The endothelial cells were isolated from human umbilical cords by mild collagenase digestion. Collagenase was obtained from Worthington Corporation, Freehole, N.J., and the general procedure is described by Jaffe, E. A., et al., 1973, *J. of Clin. Invest.*, 52:2745. The cells obtained from collagenase digestion were grown on gelatin-coated flasks in cell culture medium consisting of medium 199 (Gibco, Grand Island, N.Y.) buffered with 25 mM Hepes. The media was supplemented with 20% fetal calf serum. The media also contained 60 $\mu$g/ml solution heparin (Sigma Corporation, St. Louis, Mo.). 2 mM L-glutamine and 50 $\mu$g/ml of bovine hypothalamus extract. The bovine tissue was obtained from Pel Freeze, Rogers, Ak. The hypothalamus extract serves as a source of endothelial cell growth factor. The pH of the cell culture media was 7.4.

After the endothelial cells reached confluency, they were passaged with 0.25% trypsin containing 0.02% EDTA, and subsequently subcultured using the same solution as a base. The cells were exposed to this mixture in Hank's balanced salt solution at room temperature for about 1 minute.

Finally, approximately $2 \times 10^4$ cells/well were seeded in microtiter plates for experiments on the following day. The endothelial cell nature of the cells was confirmed both by their cobblestone morphology at confluency, and the fact that they stained positive for Factor VIII antigen by indirect immunofluorescence. The latter procedure is well known in the art, and is described by Jaffe, E. A., 1973, *J. Clin. Invest.*, 52:2745.

Monolayers of endothelial cells, prior to the fifth passage, were established on polystyrene, 96-well flat bottom micro titer plates (Corning Corporation) in Medium 199 containing 20% fetal calf serum 25 mM hepes, pH 7.4, and the other supplements described above. The surfaces of the micro titer plates were incubated with 6.4 $\mu$g/ml human plasma fibronectin for 30 minutes at 25° C. prior to plating the endothelial cells. The solution of fibronectin was removed before addition of endothelial cells.

The endothelial cell cultures were used when they were confluent. The endothelial monolayers were washed with RPMI plus 1% fetal calf serum and activated with 125 U/ml of TNF, and then incubated with labelled monocytes or polymorphonuclear leukocytes at a final concentration $5 \times 10^5$ cells per well. The cells were allowed to settle onto and bind to the endothelial cell monolayers for 30 minutes.

Human polymorphonuclear leukocytes were obtained from venus blood from several healthy adult volunteers using an anti-coagulant (10% heparin) followed by centrifugation of the blood on Ficoll-Hypaque gradients. Contaminating erythrocytes were removed by hypotonic lysis. The remaining cell population consisted of 95 to 98% polymorphonuclear leukocytes, and these cells were suspended at a concentration of $50 \times 10^6$ cells per ml in Hank's balanced salt solution, pH 7.4.

Monocytes were obtained from buffy coat preparations purchased from a blood bank. They were isolated by sequential centrifugation of the blood on Ficoll-Hypaque gradients followed by colloidal silica gradients (Sepracell). The remaining cell population consisted of 80 to 90% monocytes.

The polymorphonuclear leukocytes or monocytes were labelled with $^{111}$Indiumoxide (100 $\mu$Ci/$10^8$ PMNs) (10 mCi/mml, Amersham Corp.). Labelling occurred at room temperature in Hank's solution for 15 minutes, after which the labelled cells were isolated by centrifugation for 5 minutes, and to remove residual unincorporated label, washed twice with Hank's balanced salt solution, and then suspended in RPMI supplemented with 1% fetal calf serum.

As mentioned above, $5 \times 10^5$ of the labelled PMNs or monocytes were added per well in 96-well micro titer plates. Incubations were conducted for 30 minutes at 37° C., in a tissue culture incubator in an atmosphere of 5% $CO_2$, 95% air.

After the 30 minute incubation period, during which the polymorphonuclear leukocytes or monocytes adhere to the endothelial cell monolayer, the micro titer plates were filled and sealed with adherent transparent plastic (Dynatech, Inc., Alexander, Va.), inverted and centrifuged using a micro plate carrier, obtainable from Beckman Instruments Corp. Centrifugation was at $75 \times g$ for 5 minutes for PMNs and approximately $130 \times g$ for 5 minutes for monocytes at room temperature. This effectively removed nonadherent PMNs or monocytes from the endothelial cell monolayers. Next, the plates were blotted and aspirated dry and the number of leukocytes that remained adherent to the endothelial cell monolayers was determined using a gamma counter.

Monocytes and endothelial cells (EC) were preincubated in $\alpha_1$M for 4 hours prior to being mixed together in the assay and Table 2 shows that adhesion is inhibited (lower numbers indicate adhesion).

TABLE 2

| Alpha-1-Microglobulin Inhibits Monocyte/EC Adhesion | | | | |
|---|---|---|---|---|
| | Monocyte Donor (% Control) | | | |
| $\mu$g/ml | #65 | #67 | #54 | #57 |
| 50 | 37 | 27 | | |
| 20 | | | 72 | 66 |

TABLE 2-continued

Alpha-1-Microglobulin Inhibits Monocyte/EC Adhesion

| μg/ml | Monocyte Donor (% Control) | | | |
|---|---|---|---|---|
| | #65 | #67 | #54 | #57 |
| 5 | 62 | 47 | | |
| 4 | | | 100 | 72 |
| 0.5 | 106 | 87 | | |
| 0.8 | | | 72 | 72 |
| 0.05 | 120 | 111 | | |
| 0.16 | | | 103 | 103 |

In another type of experiment, only ECs were preincubated with $\alpha_1M$ for 4 hours and tested in the adhesion assay. Table 3 shows that adhesion was not inhibited. This was also observed when $\alpha_1$-M was present only during the adhesion period.

TABLE 3

Alpha-1-Microglobulin Incubated With EC Or During Adhesion Period Has No Effect On Monocyte/EC Adhesion

| Donor | μg/ml | Preincubated With EC (% Control) | Incubated During Adhesion (% Control) |
|---|---|---|---|
| #00 | 20 | 90 | 109 |
| | 4 | 99 | 97 |
| | 0.8 | 104 | 89 |
| | 0.16 | 98 | 90 |
| #54 | 20 | 101 | 99 |
| | 4 | 94 | 97 |
| | 0.8 | 101 | 95 |
| | 0.16 | 99 | 96 |

In the following experiment, polymorphonuclear leukocytes (PMNs) were used to test $\alpha_1M$ in the adhesion assay. The PMNs and the ECs were simultaneously preincubated for 4 hours with $\alpha_1$-M. Table 4 shows that adhesion is inhibited and was related to concentration.

TABLE 4

Alpha-1-Microglobulin Inhibits PMN/EC Adhesion After Pretreating Of Both Cell Types

| μg/ml | PMN Donor (% Control) | | | |
|---|---|---|---|---|
| | #269 | #135 | #244 | #338 |
| 20 | 60 | 122 | 40 | 41 |
| 4 | 57 | 69 | 43 | 45 |
| 0.8 | 72 | 96 | 72 | 72 |
| 0.16 | 95 | 124 | 96 | 87 |

The results of the experiments outlined in Table 5 in which either the PMNs or the ECs were preincubated show that adhesion was inhibited irrespective of which cell type was treated with $\alpha_1$-M.

TABLE 5

Alpha-1-Microglobulin Inhibits PMN/EC Adhesion After Pretreatment of Either Cell Type

| Donor | μg/ml | Preincubation With | |
|---|---|---|---|
| | | PMN (% Control) | EC (% Control) |
| #244 | 20 | 46 | 67 |
| | 4 | 62 | 70 |
| | 0.8 | 91 | 108 |
| | 0.16 | 111 | 108 |
| #338 | 20 | 47 | 62 |
| | 4 | 60 | 67 |
| | 0.8 | 94 | 100 |
| | 0.16 | 102 | 110 |

Table 6 demonstrates that $\alpha_1$-M inhibits PMN/EC adhesion if it is only present during the adhesion period (30 minutes co-incubation of PMN and EC). This is in contrast to the results in Table 3, which show that under similar conditions monocyte adhesion is unaffected.

TABLE 6

Alpha-1-Microglobulin Inhibits PMN/EC Adhesion When Present During Adhesion Period

| Donor | μg/ml | % Control |
|---|---|---|
| #160 | 125 | 56 |
| | 25 | 55 |
| | 5 | 71 |
| #321 | 125 | 54 |
| | 25 | 59 |
| | 5 | 80 |

EXAMPLE 5

Many of the materials and methods used to test the inhibitory activity of the CD 18 peptides on the chemotactic response of the polymorphonuclear leukocytes are similar or identical to those used to perform the adhesion assays described above. Polymorphonuclear leukocytes were isolated and labelled with [111]Indium as described before, and the cells were suspended in RPMI 1640 culture medium at a concentration of $5 \times 10^6$/ml. Next, 75 μl of the cell suspension and 25 μl of media containing a desired concentration of a CD 18 peptide were added to trans-well inserts, and the mixture was incubated at 37° C. for 10 minutes.

To the bottom wells of the 24-well plate 0.6 ml of media containing 0.5% zymosan-activated human serum was added. This solution was also warmed to 37° C. for 10 minutes prior to use.

Next, the assay was conducted by incubating the trans-well inserts containing the cell suspension with $\alpha_1$-M in the 24-well plates at 37° C. for 30 minutes. Subsequently, the inserts were removed, and 60 μl of a 10% sodium dodecyl sulphate solution was added to the wells of the 24-well plate. The plates were incubated with gentle shaking at room temperature for 15 minutes, and 110 μl aliquots were removed and the amount of [111]Indium determined using a gamma-counter. Table 7 shows that chemotaxis was inhibited when $\alpha_1$-M was present in the upper chamber with the neutrophil preparation.

TABLE 7

Alpha-1-Microglobulin Inhibits PMN Chemotaxis

| μg/ml | PMN Donor (% Control) | |
|---|---|---|
| | #140 | #264 |
| 20 | 54 | 84 |
| 4 | 54 | 68 |
| 0.8 | 85 | 105 |
| 0.16 | 92 | 111 |

EXAMPLE 6

The $\alpha_1$-M used above was used in the reactive inflammatory peritonitis model described above.

Four compositions were administered i.p. to mice: 1.5% thioglycollate (TG) alone; 1.5% thioglycollate and a peptide from the CD 18 adhesion molecule called 4-29 (as a positive control); 1.5% thioglycollate and a peptide from an oncogene called JUN (as a negative control); and 1.5% thioglycollate and $\alpha_1$-M. Table 8 below indicates that $\alpha_1$-M inhibits adhesion twice that of 4-29.

TABLE 8

Effect of Alpha-1-Microglobulin On Reactive Inflammatory Peritonitis

| | Avg % PMN | Avg # cells/ml ($10^4$) | Avg # PMN/ml ($10^4$) | % Inh of TG Control |
|---|---|---|---|---|
| 1.5% TG i.p. | 58 | 106 | 62 | — |
| TG + new 4–29 i.v., 0 hr (250 μg) | 41 | 79 | 32 | 48 |
| TG + JUN i.v., 0 hr (240 μg) | 63 | 73 | 46 | 26 |
| TG + A-1-M i.v., 0 hr (60 μg) | 10 | 50 | 5.3 | 91 |

SEQUENCE LISTING (1) GENERAL INFORMATION:
    (i) APPLICANT: Houston, L. L.
                  Liu, David Y.
                  Kaymakcalan, Zehra
    (ii) TITLE OF INVENTION: Method for Inhibiting Adhesion of White Blood Cells to Endothelial Cells
    (iii) NUMBER OF SEQUENCES: 18
    (iv) CORRESPONDING ADDRESS:
        (A) ADDRESSEE: Cetus Corporation
        (B) STREET: 1400 Fifty-Third Street
        (C) CITY: Emeryville
        (D) STATE: CA
        (E) COUNTRY: USA
        (F) ZIP: 94608
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/700,526
        (B) FILING DATE: 14-MAY-1991
        (C) CLASSIFICATION:
    (viii) ATTORNEY/AGENT INFORMATION:
        (A) NAME: McGarrigle Jr., Philip L.
        (B) REGISTRATION NUMBER: 31,395
        (C) REFERENCE/DOCKET NUMBER: 2600.1
    (ix) TELECOMMUNICATION INFORMATION:
        (A) TELEPHONE: (415) 420-3217
        (B) TELEFAX: (415) 658-5239
        (C) TELEX: 4992659

(2) INFORMATION FOR SEQ ID NO: 1:
    (i) SEQUENCE CHARACTERISTICS:
        (A) LENGTH: 420 amino acids
        (B) TYPE: amino acid
        (C) STRANDEDNESS: single
        (D) TOPOLOGY: linear
    (ii) MOLECULE TYPE: protein (xi) SEQUENCE DESCRIPTION: SEQ ID NO: 1:

```
Gly Gly Thr Asn Ile Asn Glu Ala Leu Leu Arg Ala Ile Phe Ile Leu
 1               5                  10                  15
Asn Glu Ala Asn Asn Leu Gly Leu Leu Asp Pro Asn Ser Val Ser Leu
            20                  25                  30
Ile Ile Leu Val Ser Asp Gly Asp Pro Thr Val Gly Glu Leu Lys Leu
        35                  40                  45
Ser Lys Ile Gln Lys Asn Val Lys Glu Asn Ile Gln Asp Asn Ile Ser
    50                  55                  60
Leu Phe Ser Leu Gly Met Gly Phe Asp Val Asp Tyr Asp Phe Leu Lys
65                  70                  75                  80
Arg Leu Ser Asn Glu Asn His Gly Ile Ala Gln Arg Ile Tyr Gly Asn
                85                  90                  95
Gln Asp Thr Ser Ser Gln Leu Lys Lys Phe Tyr Asn Gln Val Ser Thr
            100                 105                 110
Pro Leu Leu Arg Asn Val Gln Phe Asn Tyr Pro His Thr Ser Val Thr
            115                 120                 125
Asp Val Thr Gln Asn Asn Phe His Asn Tyr Phe Gly Gly Ser Glu Ile
    130                 135                 140
Val Val Ala Gly Lys Phe Asp Pro Ala Lys Leu Asp Gln Ile Glu Ser
145                 150                 155                 160
Val Ile Thr Ala Thr Ser Ala Asn Thr Gln Leu Val Leu Glu Thr Leu
                165                 170                 175
Ala Gln Met Asp Asp Leu Gln Asp Phe Leu Ser Lys Asp Lys His Ala
            180                 185                 190
```

SEQUENCE LISTING -continued

| | | | | | | | | | | | | | | |
|---|---|---|---|---|---|---|---|---|---|---|---|---|---|---|
| Asp | Pro | Asp 195 | Phe | Thr | Arg | Lys | Leu 200 | Trp | Ala | Tyr | Leu | Thr 205 | Ile | Asn | Gln |
| Leu | Leu 210 | Ala | Glu | Arg | Ser | Leu 215 | Ala | Pro | Thr | Ala | Ala 220 | Ala | Lys | Arg | Arg |
| Ile 225 | Thr | Arg | Ser | Ile | Leu 230 | Gln | Met | Ser | Leu | Asp 235 | His | His | Ile | Val | Thr 240 |
| Pro | Leu | Thr | Ser | Leu 245 | Val | Ile | Glu | Asn | Glu 250 | Ala | Gly | Asp | Glu | Arg 255 | Met |
| Leu | Ala | Asp | Ala 260 | Pro | Pro | Gln | Asp | Pro 265 | Ser | Cys | Cys | Ser | Gly 270 | Ala | Leu |
| Tyr | Tyr | Gly 275 | Ser | Lys | Val | Val | Pro 280 | Asp | Ser | Thr | Pro | Ser 285 | Trp | Ala | Asn |
| Pro | Ser 290 | Pro | Thr | Pro | Val | Ile 295 | Ser | Met | Leu | Ala | Gln 300 | Gly | Ser | Gln | Val |
| Leu 305 | Glu | Ser | Thr | Pro | Pro 310 | Pro | His | Val | Met | Arg 315 | Val | Glu | Asn | Asp | Pro 320 |
| His | Phe | Ile | Ile | Tyr 325 | Leu | Pro | Lys | Ser | Gln 330 | Lys | Asn | Ile | Cys | Phe 335 | Asn |
| Ile | Asp | Ser | Glu 340 | Pro | Gly | Lys | Ile | Leu 345 | Asn | Leu | Val | Ser | Asp 350 | Pro | Glu |
| Ser | Gly | Ile 355 | Val | Val | Asn | Gly | Gln 360 | Leu | Val | Gly | Ala | Lys 365 | Lys | Pro | Asn |
| Asn | Gly 370 | Lys | Leu | Ser | Thr | Tyr 375 | Phe | Gly | Lys | Leu | Gly 380 | Phe | Tyr | Phe | Gln |
| Ser 385 | Glu | Asp | Ile | Lys | Ile 390 | Glu | Ile | Ser | Thr | Glu 395 | Thr | Ile | Thr | Leu | Ser 400 |
| His | Gly | Ser | Ser | Thr 405 | Phe | Ser | Leu | Ser | Trp 410 | Ser | Asp | Thr | Ala | Gln 415 | Val |
| Thr | Asn | Gln | Arg 420 | | | | | | | | | | | | |

(2) INFORMATION FOR SEQ ID NO: 2:
   (i) SEQUENCE CHARACTERISTICS:
      (A) LENGTH: 117 amino acids
      (B) TYPE: amino acid
      (C) STRANDEDNESS: single
      (D) TOPOLOGY: linear
   (ii) MOLECULE TYPE: protein (xi) SEQUENCE DESCRIPTION: SEQ ID NO: 2:

| | | | | | | | | | | | | | | |
|---|---|---|---|---|---|---|---|---|---|---|---|---|---|---|
| Asn 1 | Ile | Arg | Thr | Trp 5 | Arg | Asn | Asp | Leu | Phe 10 | Gln | Leu | Gln | Lys | His 15 | Arg |
| Leu | Gln | Ile | Ala 20 | Lys | Arg | Tyr | Ile | Glu 25 | Lys | Ile | Gln | Pro | Ser 30 | Glu | Pro |
| Lys | Ile | His 35 | Ile | Phe | Asn | Glu | Arg 40 | Pro | Gly | Lys | Asp | Pro 45 | Glu | Lys | Pro |
| Glu | Ala 50 | Ser | Met | Glu | Val | Lys 55 | Gly | Gln | Lys | Leu | Ile 60 | Ile | Thr | Arg | Gly |
| Leu 65 | Gln | Lys | Asp | Tyr | Arg 70 | Thr | Asp | Leu | Val | Phe 75 | Gly | Thr | Asp | Val | Thr 80 |
| Cys | Trp | Phe | Val | His 85 | Asn | Ser | Gly | Lys | Gly 90 | Phe | Ile | Asp | Gly | His 95 | Tyr |
| Lys | Asp | Tyr | Phe 100 | Val | Pro | Gln | Leu | Tyr 105 | Ser | Phe | Leu | Lys | Arg 110 | Pro | Arg |
| Phe | Ile | Val 115 | Trp | Glu | | | | | | | | | | | |

(2) INFORMATION FOR SEQ ID NO: 3:
   (i) SEQUENCE CHARACTERISTICS:
      (A) LENGTH: 41 amino acids
      (B) TYPE: amino acid
      (C) STRANDEDNESS: single
      (D) TOPOLOGY: linear
   (ii) MOLECULE TYPE: protein (xi) SEQUENCE DESCRIPTION: SEQ ID NO: 3:

| | | | | | | | | | | | | | | |
|---|---|---|---|---|---|---|---|---|---|---|---|---|---|---|
| Met 1 | Arg | Ser | Leu | Gly 5 | Ala | Leu | Leu | Leu | Leu 10 | Leu | Ser | Ala | Cys | Leu 15 | Ala |
| Val | Ser | Ala | Gly 20 | Pro | Val | Pro | Thr | Pro 25 | Pro | Asp | Asn | Ile | Gln 30 | Val | Gln |
| Glu | Asn | Phe 35 | Asn | Ile | Ser | Arg | Ile 40 | Tyr | | | | | | | |

(2) INFORMATION FOR SEQ ID NO: 4:
   (i) SEQUENCE CHARACTERISTICS:
      (A) LENGTH: 46 amino acids
      (B) TYPE: amino acid
      (C) STRANDEDNESS: single
      (D) TOPOLOGY: linear
   (ii) MOLECULE TYPE: protein (xi) SEQUENCE DESCRIPTION: SEQ ID NO: 4:

SEQUENCE LISTING

```
Gly Lys Trp Tyr Asn Leu Ala Ile Gly Ser Thr Cys Pro Trp Leu Lys
 1           5               10              15
Lys Ile Met Asp Arg Met Thr Val Ser Thr Leu Val Leu Gly Glu Gly
             20              25              30
Ala Thr Glu Ala Glu Ile Ser Met Thr Ser Thr Arg Trp Arg
             35              40                  45
```

(2) INFORMATION FOR SEQ ID NO: 5:
    (i)    SEQUENCE CHARACTERISTICS:
        (A)    LENGTH: 25 amino acids
        (B)    TYPE: amino acid
        (C)    STRANDEDNESS: single
        (D)    TOPOLOGY: linear
    (ii)   MOLECULE TYPE: protein (xi)   SEQUENCE DESCRIPTION: SEQ ID NO: 5:

```
Lys Gly Val Cys Glu Glu Thr Ser Gly Ala Tyr Glu Lys Thr Asp Thr
 1           5               10              15
Asp Gly Lys Phe Leu Tyr His Lys Ser
             20              25
```

(2) INFORMATION FOR SEQ ID NO: 6:
    (i)    SEQUENCE CHARACTERISTICS:
        (A)    LENGTH: 39 amino acids
        (B)    TYPE: amino acid
        (C)    STRANDEDNESS: single
        (D)    TOPOLOGY: linear
    (ii)   MOLECULE TYPE: protein (xi)   SEQUENCE DESCRIPTION: SEQ ID NO: 6:

```
Lys Trp Asn Ile Thr Met Glu Ser Tyr Val Val His Thr Asn Tyr Asp
 1           5               10              15
Glu Tyr Ala Ile Phe Leu Thr Lys Lys Phe Ser Arg His His Gly Pro
             20              25              30
Thr Ile Thr Ala Lys Leu Tyr
             35
```

(2) INFORMATION FOR SEQ ID NO: 7:
    (i)    SEQUENCE CHARACTERISTICS:
        (A)    LENGTH: 34 amino acids
        (B)    TYPE: amino acid
        (C)    STRANDEDNESS: single
        (D)    TOPOLOGY: linear
    (ii)   MOLECULE TYPE: protein (xi)   SEQUENCE DESCRIPTION: SEQ ID NO: 7:

```
Gly Arg Ala Pro Gln Leu Arg Glu Thr Leu Leu Gln Asp Phe Arg Val
 1           5               10              15
Val Ala Gln Gly Val Gly Ile Pro Glu Asp Ser Ile Phe Thr Met Ala
             20              25              30
Asp Arg
```

(2) INFORMATION FOR SEQ ID NO: 8:
    (i)    SEQUENCE CHARACTERISTICS:
        (A)    LENGTH: 16 amino acids
        (B)    TYPE: amino acid
        (C)    STRANDEDNESS: single
        (D)    TOPOLOGY: linear
    (ii)   MOLECULE TYPE: protein (xi)   SEQUENCE DESCRIPTION: SEQ ID NO: 8:

```
Gly Glu Cys Val Pro Gly Glu Gln Glu Pro Glu Pro Ile Leu Ile Pro
 1           5               10              15
```

(2) INFORMATION FOR SEQ ID NO: 9:
    (i)    SEQUENCE CHARACTERISTICS:
        (A)    LENGTH: 27 amino acids
        (B)    TYPE: amino acid
        (C)    STRANDEDNESS: single
        (D)    TOPOLOGY: linear
    (ii)   MOLECULE TYPE: protein (xi)   SEQUENCE DESCRIPTION: SEQ ID NO: 9:

```
Arg Val Arg Arg Ala Val Leu Pro Gln Glu Glu Glu Gly Ser Gly Gly
 1           5               10              15
Gly Gln Leu Val Thr Glu Val Thr Lys Lys Glu
             20              25
```

(2) INFORMATION FOR SEQ ID NO: 10:
    (i)    SEQUENCE CHARACTERISTICS:
        (A)    LENGTH: 56 amino acids

SEQUENCE LISTING (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 10:

| Asp 1 | Ser | Cys | Gln | Leu 5 | Gly | Tyr | Ser | Ala | Gly 10 | Pro | Cys | Met | Gly | Met 15 | Thr |
|---|---|---|---|---|---|---|---|---|---|---|---|---|---|---|---|
| Ser | Arg | Tyr | Phe 20 | Tyr | Asn | Gly | Thr | Ser 25 | Met | Ala | Cys | Glu | Thr 30 | Phe | Gln |
| Tyr | Gly | Gly 35 | Cys | Met | Gly | Asn | Gly 40 | Asn | Asn | Phe | Val | Thr 45 | Glu | Lys | Glu |
| Cys | Leu 50 | Gln | Thr | Cys | Arg | Thr 55 | Val | | | | | | | | |

(2) INFORMATION FOR SEQ ID NO: 11:
  (i) SEQUENCE CHARACTERISTICS:
    (A) LENGTH: 58 amino acids
    (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 11:

| Ala 1 | Ala | Cys | Asn | Leu 5 | Pro | Ile | Val | Arg | Gly 10 | Pro | Cys | Arg | Ala | Phe 15 | Ile |
|---|---|---|---|---|---|---|---|---|---|---|---|---|---|---|---|
| Gln | Leu | Trp | Ala 20 | Phe | Asp | Ala | Val | Lys 25 | Gly | Lys | Cys | Val | Leu 30 | Phe | Pro |
| Tyr | Gly | Gly 35 | Cys | Gln | Gly | Asn | Gly 40 | Asn | Lys | Phe | Tyr | Ser 45 | Glu | Lys | Glu |
| Cys | Arg 50 | Glu | Tyr | Cys | Gly | Val 55 | Pro | Gly | Asp | | | | | | |

(2) INFORMATION FOR SEQ ID NO: 12:
  (i) SEQUENCE CHARACTERISTICS:
    (A) LENGTH: 10 amino acids
    (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 12:

| Gly 1 | Asp | Glu | Glu | Leu 5 | Leu | Arg | Phe | Ser | Asn 10 |
|---|---|---|---|---|---|---|---|---|---|

(2) INFORMATION FOR SEQ ID NO: 13:
  (i) SEQUENCE CHARACTERISTICS:
    (A) LENGTH: 20 amino acids
    (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 13:

| Gly 1 | Pro | Val | Pro | Pro 5 | Pro | Asp | Asn | Ile | Gln 10 | Val | Gln | Glu | Asn | Phe 15 | Ile |
|---|---|---|---|---|---|---|---|---|---|---|---|---|---|---|---|
| Ser | Ile | Tyr | Gly 20 | | | | | | | | | | | | |

(2) INFORMATION FOR SEQ ID NO: 14:
  (i) SEQUENCE CHARACTERISTICS:
    (A) LENGTH: 16 amino acids
    (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 14:

| Pro 1 | Pro | Asp | Asn | Ile 5 | Gln | Val | Glu | Glu | Asn 10 | Phe | Ile | Ser | Ile | Tyr 15 | Gly |
|---|---|---|---|---|---|---|---|---|---|---|---|---|---|---|---|

(2) INFORMATION FOR SEQ ID NO: 15:
  (i) SEQUENCE CHARACTERISTICS:
    (A) LENGTH: 20 amino acids
    (B) TYPE: amino acid
    (C) STRANDEDNESS: single
    (D) TOPOLOGY: linear
  (ii) MOLECULE TYPE: protein (xi) SEQUENCE DESCRIPTION: SEQ ID NO: 15:

| Ala | Val | Leu | Pro | Gln | Glu | Glu | Glu | Gly | Gly | Gly | Gly | Gln | Leu | Val | Thr |
|---|---|---|---|---|---|---|---|---|---|---|---|---|---|---|---|

-continued

SEQUENCE LISTING

```
          1               5              10              15
Lys Lys Glu Asp
         20
```

(2) INFORMATION FOR SEQ ID NO: 16:
   (i) SEQUENCE CHARACTERISTICS:
     (A) LENGTH: 15 amino acids
     (B) TYPE: amino acid
     (C) STRANDEDNESS: single
     (D) TOPOLOGY: linear
   (ii) MOLECULE TYPE: protein (xi) SEQUENCE DESCRIPTION: SEQ ID NO: 16:
```
Thr Glu Val Thr Lys Lys Glu Asp Ser Ser Gln Leu Leu Gly Tyr
 1               5                  10                  15
```

(2) INFORMATION FOR SEQ ID NO: 17:
   (i) SEQUENCE CHARACTERISTICS:
     (A) LENGTH: 7 amino acids
     (B) TYPE: amino acid
     (C) STRANDEDNESS: single
     (D) TOPOLOGY: linear
   (ii) MOLECULE TYPE: protein (xi) SEQUENCE DESCRIPTION: SEQ ID NO: 17:
```
Gly Met Thr Ser Arg Tyr Asn
 1               5
```

(2) INFORMATION FOR SEQ ID NO: 18:
   (i) SEQUENCE CHARACTERISTICS:
     (A) LENGTH: 15 amino acids
     (B) TYPE: amino acid
     (C) STRANDEDNESS: single
     (D) TOPOLOGY: linear
   (ii) MOLECULE TYPE: protein (xi) SEQUENCE DESCRIPTION: SEQ ID NO: 18:
```
Val Thr Glu Val Thr Lys Lys Glu Asp Ser Gln Leu Gly Tyr Ser
 1               5                  10                  15
```

The present invention has been described with reference to specific embodiments. However, this application is intended to cover those changes and substitutions which may be made by those skilled in the art without departing from the spirit and the scope of the appended claims.

We claim:

1. A method for altering white blood cell adhesion to endothelial cells comprising administering a therapeutically effective amount of $\alpha_1 M$ or fragments thereof, to a mammal.

2. A method in accordance with claim 1, wherein the endothelial cells are positioned on the inside of a blood vessel.

3. A method in accordance with claim 2, wherein the compound is administered to between 10 and 5,000 µg/ml blood.

4. A method in accordance with claim 2, wherein the white blood cells are monocytes, neutrophils and lymphocytes.

5. A method for therapeutically treating sepsis, inflammation, or arthritis in a human subject comprising administering a therapeutically effective amount of $\alpha_1 M$ to reduce white blood cell adhesion to endothelial cells and to prevent the migration of white blood cells through blood vessel walls into tissues.

6. A method in accordance with claim 1 wherein the compound is administered to between 100 and 500 µg/ml blood.

7. A pharmaceutical composition to reduce white blood cell adhesion to endothelial cells comprising a therapeutically effective amount of $\alpha_1 M$ and a pharmaceutically acceptable, aqueous carrier.

* * * * *